United States Patent [19]

Matkovich

[11] Patent Number: 5,451,321

[45] Date of Patent: * Sep. 19, 1995

[54] VENTING SYSTEM

[75] Inventor: Vlado I. Matkovich, Glen Cove, N.Y.

[73] Assignee: Pall Corporation, East Hills, N.Y.

[*] Notice: The portion of the term of this patent subsequent to Jun. 30, 2009 has been disclaimed.

[21] Appl. No.: 820,608

[22] PCT Filed: May 24, 1991

[86] PCT No.: PCT/US91/03616

§ 371 Date: Nov. 18, 1992

§ 102(e) Date: Nov. 18, 1992

Related U.S. Application Data

[63] Continuation-in-part of Ser. No. 528,160, May 24, 1990, Pat. No. 5,126,054.

[51] Int. Cl.$^6$ .................................................. B01D 61/58
[52] U.S. Cl. ...................................... 210/641; 210/436
[58] Field of Search ............... 210/321.85, 436, 472, 210/188, 641, 445, 446

[56] References Cited

U.S. PATENT DOCUMENTS

| | | | |
|---|---|---|---|
| 2,781,064 | 2/1957 | Dawkins | 141/54 |
| 3,149,758 | 9/1964 | Bush et al. | 222/189 |
| 3,364,658 | 1/1968 | Walker | 55/171 |
| 3,394,533 | 7/1968 | Li et al. | 55/337 |
| 3,523,408 | 8/1970 | Rosenberg | 55/159 |
| 3,631,654 | 1/1972 | Riely et al. | 55/159 |
| 3,650,093 | 3/1972 | Rosenberg | 55/159 |
| 3,705,100 | 12/1972 | Blatt et al. | 210/321.85 X |
| 3,803,810 | 4/1974 | Rosenberg | 55/159 |
| 3,892,236 | 7/1975 | Djerassi | 128/214 R |
| 4,126,558 | 11/1978 | Luceyk | 210/429 |
| 4,136,796 | 1/1979 | Dubois | 220/256 |
| 4,223,695 | 9/1980 | Muetterties | 137/173 |
| 4,276,170 | 6/1981 | Vaillancourt | 210/436 |
| 4,294,594 | 10/1981 | Sloane, Jr. et al. | 55/186 |
| 4,360,435 | 11/1982 | Bellamy et al. | 210/636 |
| 4,411,866 | 10/1983 | Kanno | 422/25 |
| 4,459,139 | 7/1984 | vonReis et al. | 55/189 |
| 4,635,467 | 1/1987 | Hoffa et al. | 73/16 |
| 4,734,269 | 3/1988 | Clarke et al. | 210/422 X |
| 4,900,308 | 2/1990 | Verkaart | 604/126 |
| 4,915,847 | 4/1990 | Dillon et al. | 210/737 |
| 4,997,577 | 3/1991 | Stewart | 210/767 |
| 5,074,839 | 12/1991 | Choksi et al. | 604/4 |
| 5,079,168 | 1/1992 | Amiot | 437/284 |
| 5,126,054 | 6/1992 | Matkovich | 210/641 |
| 5,180,504 | 1/1993 | Johnson et al. | 210/767 |
| 5,403,304 | 4/1995 | Ishida | 604/403 |

FOREIGN PATENT DOCUMENTS

| | | |
|---|---|---|
| 2012677 | 9/1990 | Canada . |
| 0090093 | 10/1983 | European Pat. Off. . |
| 0183057 | 6/1986 | European Pat. Off. . |
| 0302722 | 2/1989 | European Pat. Off. . |
| 0455215 | 11/1991 | European Pat. Off. . |
| 1221625 | 2/1971 | United Kingdom . |
| 1585989 | 3/1981 | United Kingdom . |
| 8602825 | 5/1986 | WIPO . |

Primary Examiner—Frank Spear
Attorney, Agent, or Firm—Leydig, Voit & Mayer

[57] ABSTRACT

Biological fluid processing assemblies having a gas inlet and/or a gas outlet are disclosed.

60 Claims, 8 Drawing Sheets

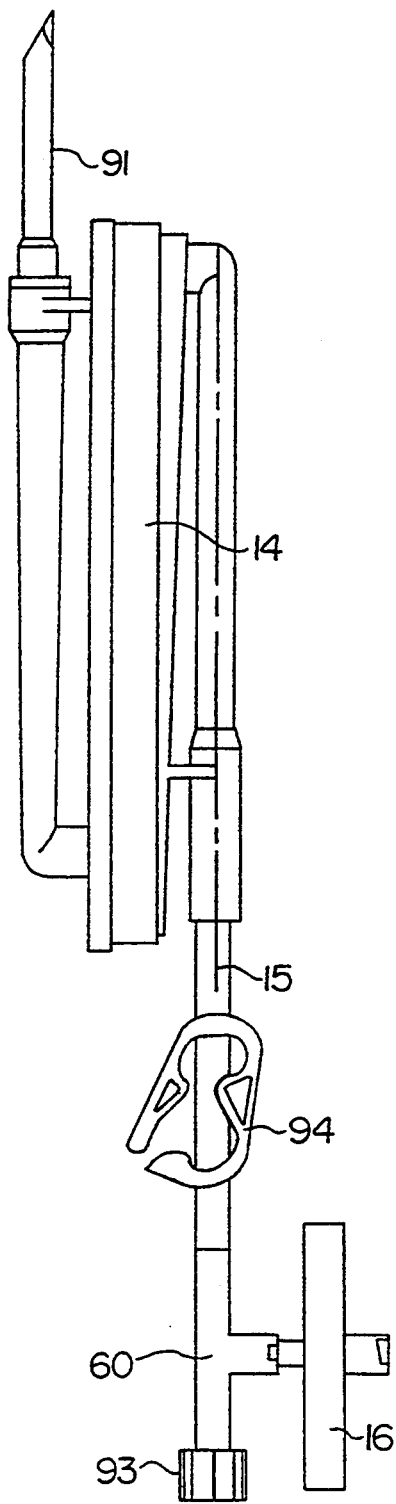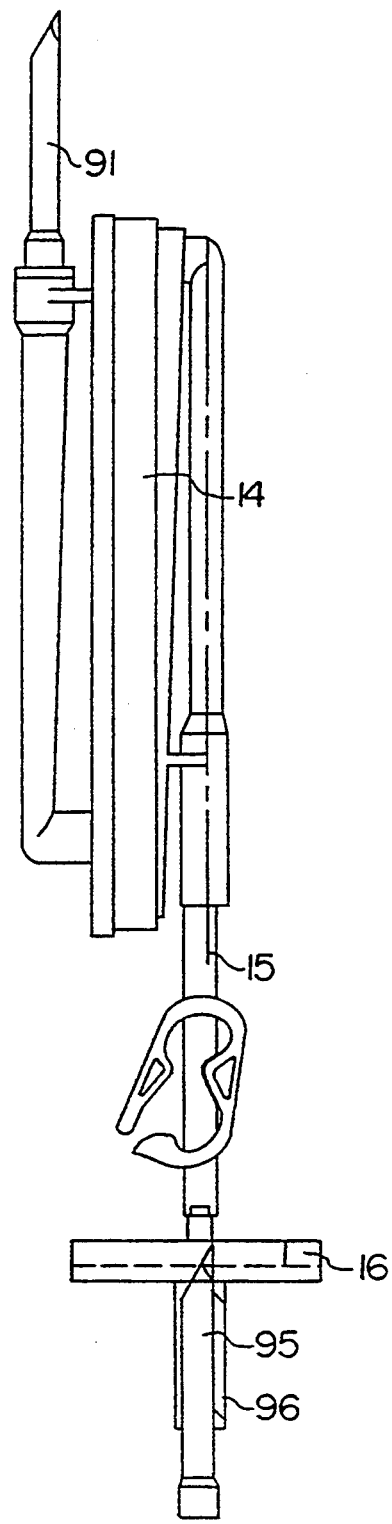
FIG. 9A
FIG. 9B ated (CPDA-1) system,
VENTING SYSTEM

This application is a continuation-in-part of application Ser. No. 07/528,160, filed May 24, 1990, now U.S. Pat. No. 5,126,054, and it is the U.S. National Phase of PCT international application No. PCT/US91/03616 filed May 24, 1991.

TECHNICAL FIELD

The present invention relates to a system for processing donated blood into its therapeutically valuable blood components and derivative therapy, and more particularly to improved methods and means for venting air and other gases entrapped in a blood processing system, and to improved methods and means for the recovery of substantially all of the blood products derived from the donated blood.

BACKGROUND OF THE INVENTION

The development of plastic blood collection bags has facilitated the separation of donated whole blood into its various components and analogous products, including factors, concentrates, and therapeutic serum, thereby making these different blood products available as a transfusion product. The separation of a single unit of donated whole blood, about 450 milliliters in USA practice, into its components is typically accomplished by use of differential sedimentation using centrifugation, as is well known to those skilled in the art.

A typical procedure used in the United States, the citrate-phosphate-dextrose-adenine (CPDA-1) system, utilizes a series of steps to separate donated blood into three components, each component having substantial therapeutic and monetary value. The procedure typically utilizes a blood collection bag which is integrally attached via flexible tubing to at least one, and preferably two or more, satellite bags. Using centrifugation, whole blood may be separated by differential sedimentation into such valuable blood components as plasma, packed red cells (PRC), platelet-rich plasma (PRP), platelet Concentrate (PC), and cryoprecipitate (which may require extra processing in order to obtain). The plasma may itself be transfused into a patient, or it may be separated by complex processes into a variety of other valuable blood products.

With the passage of time and the accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

For this reason, the separation of blood into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels; associated internal and external bleeding additionally requires more frequent transfusions of PC, and this has caused platelets to be in short supply and has put pressure on blood banks to increase platelet yield per unit of blood.

One of the problems attendant with the separation of various blood components using a multiple bag system and centrifugation is that highly valuable blood components become trapped in the conduits connecting the various bags and in the various biomedical devices that may be used in the system. It is an object of this invention to provide apparatuses and methods which permit the recovery of these valuable blood components.

In blood processing systems, air, in particular oxygen, present in stored blood and blood components, or in the storage container, may lead to an impairment of the quality of the blood components and may decrease their storage life. More particularly, oxygen may be associated with an increased metabolic rate (during glycolysis), which may lead to decreased storage life, and decreased viability and function of whole blood cells. For example, during storage red blood cells metabolize glucose, producing lactic and pyruvic acids. These acids decrease the pH of the medium, which in turn decreases metabolic functions. Furthermore, the presence of air/gas in the satellite bag may present a risk factor to a patient's being transfused with a blood component. For example, as little as 5 ml may cause severe injury or death. Despite the deleterious effect of oxygen on storage life and the quality of blood and blood components, the prior art has not addressed the removal of gases from blood processing systems during the initial collection and processing steps. It is, therefore, an object of this invention to provide a sterile blood processing system in which gases present in the system are separated from the blood or blood product.

Another problem has been maintaining the sterility of the processing system. The word sterility, as used herein, refers to maintaining a system free from viable contaminating microorganisms. Exemplary methods of determining sterility include tests using fluid thioglycollate medium or using soybean-casein digest medium, described in more detail in the U.S. Code of Federal Regulations (21 CFR 610.12).

SUMMARY OF THE INVENTION

In accordance with one aspect of the present invention, there is provided a blood processing system which includes means for removing gas from the various components of the system in order to improve the storage life; safety, and high quality of the processed blood.

In accordance with another aspect of this invention, a blood processing system is provided wherein liquid trapped in various elements of the blood processing system is recovered either by causing a volume of gas behind the entrapped liquid to push the liquid through those elements and into the designated collection bag, or by pulling the entrapped liquid into the designated collection bag by a pressure differential (e.g., gravity head, pressure cuff, suction, and the like).

In accordance with yet another aspect of the invention, it will be appreciated that a means of the present invention is useful in any liquid transfer or delivery system where there is to be a one time removal of gases from the system and the ingress of gases into the system during liquid transfer or delivery is to be prevented, including, for example, such systems that are to be primed for future liquid transfer or systems that are to be filled to a predetermined level.

The gas inlet and gas outlet of the present invention is particularly well adapted for use in pharmaceutical and medicinal applications, and in medical and pharmaceutical devices; an embodiment of the invention is particularly suited for use in devices where gases present in such systems must be vented or where gases must be prevented from reaching a patient receiving an injection of the liquid.

BRIEF DESCRIPTION OF THE DRAWINGS

FIG. 3A multiple gas storage means and 3B, a single gas storage means.

FIG. 9 is an administration assembly including a functional biomedical device and a gas outlet.

DESCRIPTION OF THE PREFERRED EMBODIMENTS

The present invention primarily involves a sterile blood processing system for the post-donation processing of donated blood into valuable blood products. However, it is intended that the invention is not to be limited by the type of fluid being processed or administered. Any biological fluid, such as a saline solution, a medicant solution, or a nutrient solution, which are processed or administered using devices or assemblies which contain or collect air or gas, are included within the scope of the present invention. Below, the invention will be described using blood or a blood product as the biological fluid, but it should be evident that other biological fluids may be incorporated into the blood processing or administration systems described herein.

In the present invention, means and methods are provided to remove air, oxygen, and other gases from a system in order to minimize the volume of gases that remain in, or in contact with, a blood product during storage. Means and methods are also provided for the recovery of valuable blood and blood products that may become entrapped in the various elements of the system during blood processing and which would otherwise be lost.

The gas outlet may be any of a variety of means and devices which are capable of separating gas such as air, oxygen and the like, that may be present in a blood processing system from the liquid, i.e., blood and/or blood components that are processed in the system. The gas inlet may be any of a variety of means and devices which are capable of allowing gas, such as air, oxygen, and the like, into a processing system. As used herein, gas refers to any gaseous fluid, such as air, sterilized air, oxygen, carbon dioxide, and the like; it is intended that the invention is not to be limited thereby.

Additionally, the gas inlet and gas outlet are chosen so that the sterility of the system is not compromised. The gas inlet and the gas outlet are particularly suited for use in closed systems, or within about 24 hours of a system being opened. Suitable gas inlet and gas outlet include a liquophobic porous medium with a sufficiently small pore size to preclude the ingress of bacteria into the system. Because the liquophobic porous medium is not wettable by the blood and blood product being processed in the system, gas in the system that contacts the liquophobic medium will pass through it and the blood or blood products will not be absorbed by the liquophobic porous medium. Typically, the pore size of the liquophobic porous medium will be less than 0.2 microns to provide a satisfactory bacterial barrier.

Figure 1:
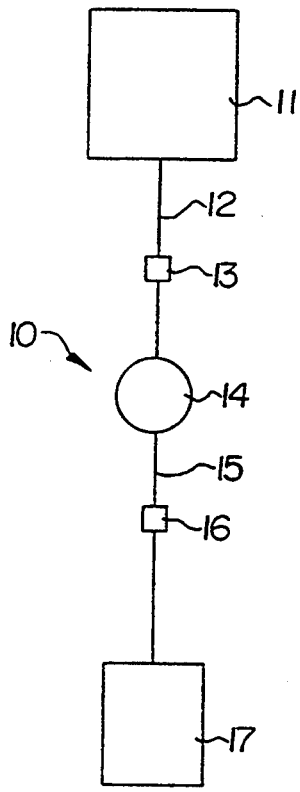
FIG. 1 is an embodiment of a blood processing system which includes a gas inlet and a gas outlet in the conduits in sealed communication with the bags, according to the invention.
Figure 2:
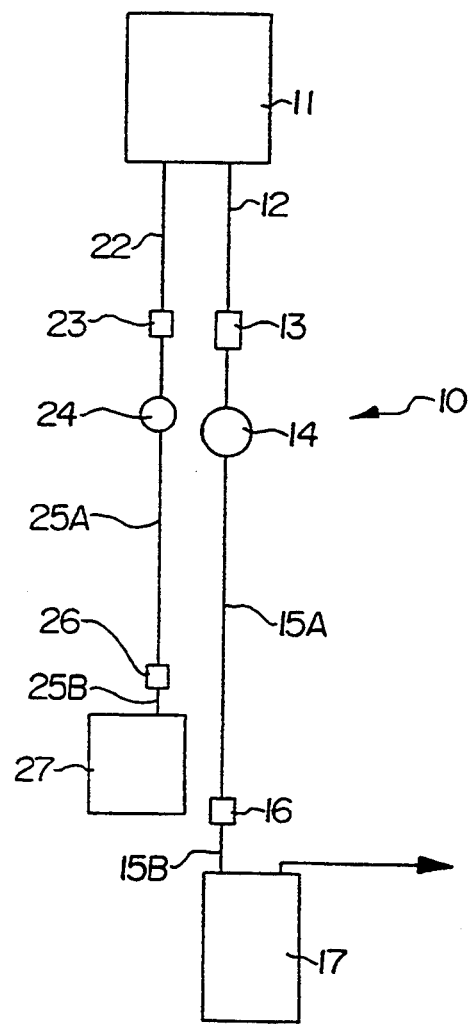
FIG. 2 is another embodiment of a blood processing system according to the invention, illustrating a blood collection system for separating whole blood into packed red cells, platelet concentrate, and plasma.
Figure 3A:
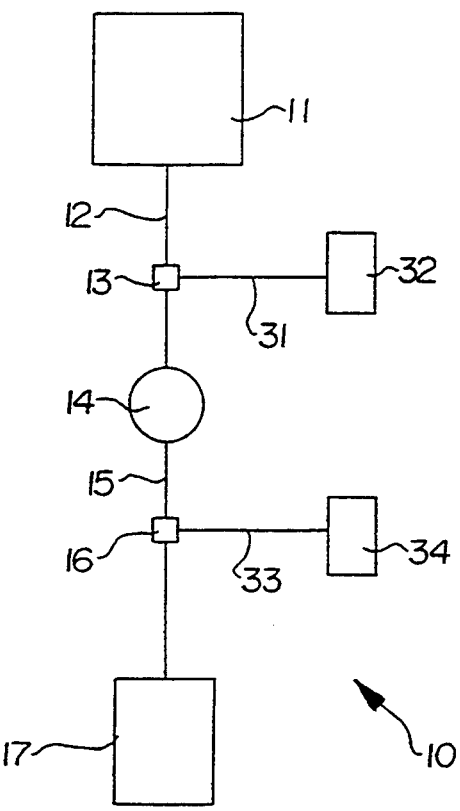
FIGS. 3A and 3B are embodiments of a blood processing system according to the invention which include gas inlet and gas outlet in sealed communication with separate gas storage means.

Typical blood processing assemblies include at least two containers connected by a conduit (see for example, FIGS. 1 and 3). While at least one gas inlet or gas outlet may be interposed between such a simple two bag system, it is more likely that the venting means in accordance with the invention will be more useful in more complicated processing systems, having for example, one or more functional biomedical devices, such as a separatory or filter device, interposed between the containers (see for example, FIGS. 2 and 4).

Figure 5:
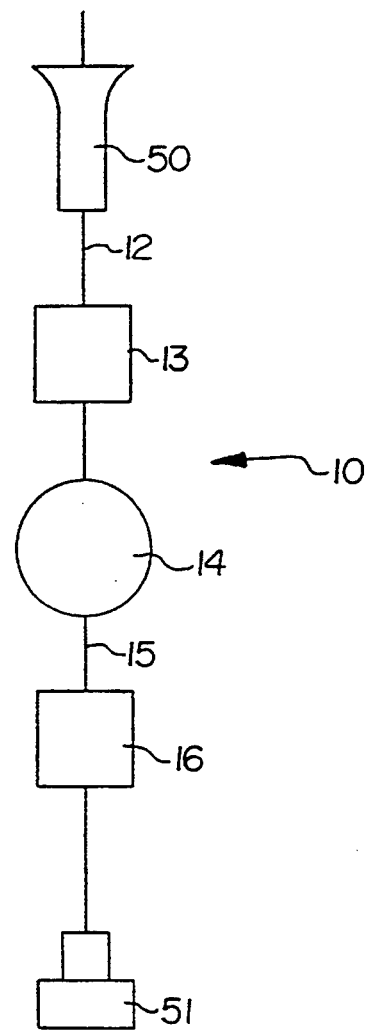
FIG. 5 is a modified assembly including connector means on each end of a conduit having a gas inlet, a functional biomedical device, and a gas outlet.

In its simplest aspect, the present invention involves a blood processing assembly comprising a conduit, a gas inlet and/or a gas outlet in the conduit, and a functional biomedical device. See, for example, FIG. 5. This embodiment of the invention may have a needle or the like attached to one end of the conduit so that the assembly may be used, for example, as an intravenous feeding device. This embodiment may also be configured, as illustrated in FIGS. 5 and 9, with a connector means on an end or ends of the assembly.

In other, more complex aspects, the present invention may involve a blood processing assembly comprising a first container and a second container, and a conduit interconnecting the first container with the second container; and, optionally, at least one third container and a conduit interconnecting the first container with the third container; and having interposed between the first container and a second container, at least one functional biomedical device; and having interposed between the first container and the second container, at least one gas inlet or gas outlet.

With the increased acceptance of transfusion therapy in the treatment of a number of disorders and conditions, physicians have found it necessary or desirable to transfuse multiple blood units, each of which is typically leucocyte-depleted during administration. Whether the administration set comprises multiple bags and a single high capacity leucocyte filter, or multiple bags and multiple filters, gas in the administration assembly may present a substantial risk. Thus, in accordance with another embodiment of the invention, a typical administration assembly includes a first conduit having a spike or the like on one end and a functional biomedical device, such as a leucocyte depletion filter, on the other end. A second conduit leads from the biomedical device and typically has a connector on the downstream end. In accordance with the present invention, a gas outlet is disposed in the second conduit downstream of the biomedical device; and a gas inlet may be disposed in the first conduit between the spike and the biomedical device. It is further preferred that the assembly includes a preprimed functional biomedical device.

Pre-priming, as used herein, refers to wetting or priming the inner surfaces of an assembly prior to its actual use. For example, using the device illustrated in FIG. 9a, the spike may be inserted into a solution container; the clamp is opened to allow fluid to flow through the assembly; then, with the passage of fluid through the assembly, gas downstream of the fluid is expelled through the gas outlet until fluid reaches the branching element, at which point the clamp is closed. With the clamp in a closed position, the connector downstream of the gas outlet may be opened or readied for use without fluid in the assembly dripping through the connector.

According to another embodiment of the invention, a gas inlet or a gas outlet may be disposed in a conduit having a connector on both ends. In this way, the embodiment may be inserted into a previously existing system. For example, if one of the connectors is a spike, the spike can be inserted into a container; in this way a fluid flow path may be established which is capable of utilizing a gas inlet or a gas outlet in any of the ways described in accordance with this invention. One embodiment of such an assembly is illustrated in FIG. 5, in which spike 50 and connector 51 may be used to attach the assembly to a pre-existing fluid processing or administration set. In another embodiment, illustrated in FIG. 9b, a component may be easily and aseptically added to a pre-existing fluid processing or administration set: a spike connector leading from a medication container or the like may be inserted into a previously existing assembly by inserting the spike through a gas inlet or gas outlet of the invention. In this embodiment, the spike penetrates the membrane, establishing an aseptic connection.

Blood, as used herein, refers to the following: whole blood; anti-coagulated whole blood (AWB); packed red cells (PRC) obtained from AWBF platelet-rich plasma (PRP) obtained from AWB; platelet concentrate (PC) obtained from AWB or PRP; plasma obtained from AWB or PRP; red cells separated from plasma and resuspended in physiological fluid; cryoprecipitate; platelets separated from plasma and resuspended in physiological fluid; and any of the above mixed with or suspended in a physiological fluid. As used herein, blood refers to the components described above, and to similar or analogous blood products obtained from any of the above, or by other means, or with similar properties. In accordance with the invention, each of these blood products may be processed in the manner described herein.

A functional biomedical device, as used herein, may be any of a number of devices or assemblies in which air or gases are present and/or may collect or form, or should be displaced prior to use of the assembly. Exemplary functional biomedical devices include a filter, such as a leucocyte depletion filter; a separatory device, such as a platelet concentrator, preferably a non-centrifugal platelet concentrator; a debubbler; a pump; and a connector. The functional biomedical device may also include a device for destroying biological contaminants, such as a high intensity light wave chamber, or a device for sampling a biological liquid.

Figure 3B:
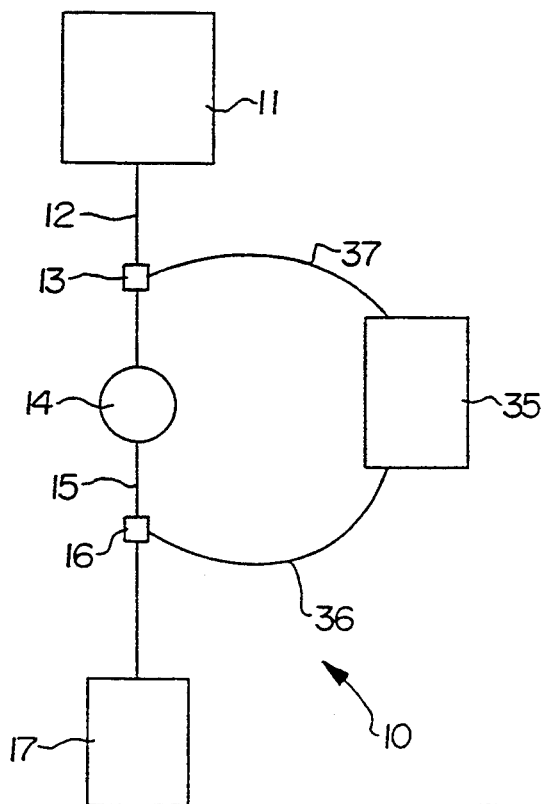

In accordance with the invention, a clamp, closure, or the like may be positioned on or in any or all of the conduits in order to facilitate a desired function, i.e., establishing a desired flow path for blood product or gas. For example, when processing a blood product through a system such as is illustrated in FIG. 3B, during the removal of gases from conduit 12, functional biomedical device 14 and conduit 15, it may be desirable to clamp conduit 15 immediately below gas outlet 16 and to clamp conduit 37 immediately above gas storage means 35. When it is desirable to use the gas in gas storage means 35 to maximize the recovery of blood product, the clamp below gas outlet 16 is released, a clamp adjacent to gas storage means 35 in conduit 36 is closed, a clamp in conduit 37 adjacent to gas storage means 35 is opened, and a clamp in conduit 37 adjacent to gas intake means 13 is opened.

In accordance with the invention, the processing system is provided with a gas inlet to permit the introduction of air or gas into the system after most of the processing has taken place, and/or with a gas outlet to permit gases in the various elements of the system to be separated from the liquid to be processed. It is intended that gas inlet and the gas outlet may both be used in a blood processing system, or the respective gas inlet or gas outlet may be used alone.

To that end, a gas inlet or gas outlet may be included in any of the various elements of the assembly. By way of illustration, gas inlet or gas outlet may be included in at least one of the conduits which connect the different containers, in a wall of the containers that receive the processed blood and/or blood product, or in a port on or in one of those containers. The gas inlet or gas outlet may also be included on or in a combination of the elements mentioned above. Also, a functional biomedical device may include one or more gas inlet or gas outlet. Generally, however, it is preferred to include a gas inlet or gas outlet in the conduits which connect the containers or in the functional medical device. Included within the scope of the invention is the use of more than one gas inlet or gas outlet in any one conduit, in any one blood product receiving container, or in a functional biomedical device.

It will be apparent to one skilled in the art that the placement of a gas inlet or a gas outlet may be optimized to achieve a desired result. For example, it may be desirable to locate the gas inlet upstream of the functional medical device and in or as close to the first container as is practical in order to maximize the recovery of blood product. Also, it may be desirable to locate the gas outlet downstream of the functional biomedical device and as close to the blood product receiving container as is possible in order to maximize the volume of gas that is removed from the system.

Such placement of the gas inlet or gas outlet is particularly desirable where there is only one gas inlet or gas outlet in the system.

The gas inlet and the gas outlet is a porous medium designed to allow gas to pass therethrough. For the sake of convenience and clarity, the porous medium in the gas inlet or gas outlet shall be referred to hereinafter as a membrane.

As used herein, connector refers to any structure used to form a joint or to join itself to another piece. These connectors establish a flow path through various elements of an assembly or system. Connector, as used herein, refers to penetrating connectors, such as a spike, cannula, or needle; and mating connectors, such as Luer-type, screw-type, friction-type, or connectors which are bonded together.

In accordance with the invention, blood product recovery from the various elements of the blood processing system may be maximized. After centrifugation of the blood, the separate fractions of blood components are expressed to their respective receiving containers through the appropriate conduits and functional biomedical devices, if any. Blood product that has become entrapped in these elements during processing may be recovered either by passing purge gas through the conduits and biomedical devices or by drawing at least a partial vacuum on the system so as to draw out the entrapped liquid and to permit it to drain into the appropriate receiving container. The purge gas may be provided from any of a number of sources. For example, the blood processing system may be provided with a storage container for the storage of the purge gas, the purge gas may be the gas that is removed from the system during the blood processing function, or the purge may be injected aseptically into the system from an outside source (e.g., through a syringe). For example, it may be desirable to use sterile purge gas that has been sterilized in a separate container apart from the blood processing system.

The gas inlet of the present invention preferably includes a microporous membrane in a housing. The gas inlet may comprise a microporous membrane having both liquophobic and liquophilic layers, as described below, or may comprise other structures which allow gas to enter the system, but do not allow contaminants to enter. In a preferred embodiment, the microporous membrane is preferably liquophobic, that is, it is non-wettable. The membrane may also be liquophilic, but means should be included to keep the liquophilic membrane dry until ready for use. For example, while the blood product is being processed through the system, a clamp or other closure mechanism (such as a cap or sufficient pressure differential) may be used to avoid wetting the liquophilic membrane. By liquophilic is meant that the microporous membrane layer is wetted by the liquid being processed. The liquophilic membrane is capable of passing gas therethrough so long as it remains unsaturated by the liquid being processed.

The term liquophobic as used herein is effectively the obverse of the term liquophilic; that is, a porous liquophobic material has a critical wetting surface tension lower than the surface tension of the applied liquid and is not readily or spontaneously wetted by the applied liquid. Liquophobic materials may be characterized, then, by a high contact angle between a drop of liquid placed on the surface, and the surface. Such high contact angle indicates poor wetting.

In accordance with the invention, gas may be removed from the blood processing assembly or from in contact with a blood or blood product by passing the air or gas through a gas outlet. The gas outlet may comprise a liquophobic membrane as described above, or may comprise other structures which allow gas to pass, but do not allow contaminants to enter. In a preferred embodiment, the gas outlet includes a multi-layer microporous membrane in a housing. The first layer of the microporous membrane is liquid-wettable, i.e., liquophilic, as noted above. The liquophilic membrane is capable of passing gas therethrough so long as it remains unsaturated by the liquid being processed. The second microporous membrane layer is not wettable by the liquid being processed by the delivery system, that is, the second layer is liquophobic.

The liquophilic layer of the multi-layer microporous membrane is preferably positioned in the housing to the inward side of the gas outlet so that the liquophilic layer is in direct communication with a conduit in which the gas outlet is to be carried. In this way the liquophilic layer is the first layer to be contacted either by gas that is to be passed from the liquid transfer or delivery system or by the liquid being transferred or delivered by the system.

The liquophobic layer is also capable of passing gas therethrough. The liquophobic layer may be superimposed on the liquophilic layer, preferably positioned on the outward side of the gas outlet. The liquophobic layer is thus not contacted by either gas or liquid in the delivery system until the gas or liquid has passed through the liquophilic layer. Because of the liquid-wettable character of liquophilic layer and the non-wettable character of liquophobic layer, gas that contacts the gas outlet passes through the gas outlet so long as the liquophilic layer remains unwetted by liquid. Once the liquophilic layer becomes wetted with liquid, gas is no longer able to pass through the liquophilic layer so the gas outlet becomes sealed or inactivated. Accordingly, after the liquophilic layer is wetted by the liquid being processed, gas from outside the delivery system is foreclosed from entering the system through the gas outlet. The combined liquophobic and liquophilic membrane is particularly advantageous when the gas outlet is used in a closed sterile system; once any gases present in the system are vented, unwanted gases cannot reenter the closed system through the gas outlet.

It will be appreciated that the liquophilic and liquophobic layers may be two separate layers, or they may be bonded together. In addition, the invention contemplates the use of a plurality of separate membrane elements combined together to form the liquophilic microporous membrane and the use of a plurality of separate membrane elements combined together to form the liquophobic microporous membrane. By the term plurality is meant two or more. The plurality of separate membrane layers may be individually prepared and bonded together by various means known to those skilled in the art. For example, the separate membrane layers may be bonded together by drying two or more layers maintained in close contact. Alternatively, by way of illustration and not in limitation, the separate membrane layers may be prepared by passing the material used to form the membrane over a hot drum, against which the membrane is firmly held by a tensioned felt web or other process sheet. In addition, it is likewise possible to combine a suitable supporting substrate with the membrane layer, if desired, and the supporting substrate may serve as a permanent support.

In accordance with the invention the liquophobic microporous membrane must have sufficient liquophobicity with respect to the liquid to be processed in the liquid delivery or transfer system such that it will prevent the intrusion of the liquid being processed into the membrane. On the other hand the liquophilic microporous membrane must have a pore size and sufficient liquophilicity with respect to the liquid to be processed such that it will be wetted by the liquid sufficiently to prevent the passage of gas after it is wetted. It is preferred that both the liquophilic and liquophobic microporous membranes have, when combined for use in the gas outlet, an overall pore size such that the membranes form a bacterial barrier. When the pore size of the microporous membranes is so chosen, the intrusion of bacteria into the system through the gas outlet is prevented. It will be readily appreciated that a gas outlet so configured is particularly well adapted for a closed system and/or for sterile liquid processing systems. Preferably, particularly in medical applications, the system is gamma-sterilizable. Such gas outlet can even be used without a cap, if desired, although it is within the purview of the invention to cap the gas outlet if desired.

The microporous membrane may be made from a variety of materials. The gas inlet and the gas outlet are porous media designed to allow gas to pass therethrough. A variety of materials may be used to form the porous media provided the requisite properties of the particular porous medium are achieved. These include the necessary strength to handle the differential pressures encountered in use and the ability to provide the desired filtration capability while providing the desired permeability without the application of excessive pressure. In a sterile system, the porous medium should also preferably have a pore rating of 0.2 micrometer or less to preclude bacteria passage. The porous medium may be, for example, a porous fibrous medium, such as a depth filter, or a porous membrane or sheet. Multilayered porous media may be used, for example, a multilayered porous membrane with one layer being liquophobic and the other liquophilic.

Preferred starting materials are synthetic polymers including polyamides, polyesters, polyolefins, particularly polypropylene and polymethylpentene, perfluorinated polyolefins, such as polytetrafluoroethylene, polysulfones, polyvinylidene difluoride, polyacrylonitrile and the like, and compatible mixtures of polymers. The most preferred polymer is polyvinylidene difluoride. Within the class of polyamides, the preferred polymers include polyhexamethylene adipamide, poly-$\epsilon$-caprolactam, polymethylene sebacamide, poly-7-aminoheptanoamide, polytetramethylene adipamide (nylon 46), or polyhexamethylene azeleamide, with polyhexamethylene adipamide (nylon 66) being most preferred. Particularly preferred are skinless, substantially alcohol-insoluble, hydrophilic polyamide membranes, such as those described in U.S. Pat. No. 4,340,479.

Other starting materials may also be used to form the porous media of this invention including cellulosic derivatives, such as cellulose acetate, cellulose propionate, cellulose acetate-propionate, cellulose acetate-butyrate, and cellulose butyrate. Non-resinous materials, such as glass fibers, may also be used.

It will be appreciated that if the material chosen is normally liquophobic, and it is desired to use this material for the liquophilic microporous membrane, then the normally liquophobic material will have to be treated so as to make it liquophilic. The nature of the material used to make the membranes, the compatibility of the materials chosen for the membranes with one another and with the liquid to be processed all are factors to be considered in selecting a particular material for a membrane for a given end application. However, quite apart from those considerations, it is generally desirable and preferable that the same material be used for both the liquophilic microporous membrane and for the liquophobic microporous membrane so as to facilitate the bonding of the two different membranes to one another, if desired, as is preferred.

As noted above, the preferred material for both the liquophilic microporous membrane and the liquophobic microporous membrane is polyvinylidene difluoride. Since polyvinylidene difluoride is liquophobic, it must be treated in order to render it liquophilic. Various treatments of the normally liquophobic polyvinylidene difluoride to render it liquophilic are known. However, the preferred method for making the polyvinylidene difluoride material liquophilic is to treat a liquophobic polyvinylidene difluoride microporous membrane by subjecting it to gamma radiation in the presence of a liquophilic agent, such as, for example, hydroxyethylmethacrylate (EEMA). Preferably liquophilic and liquophobic polyvinylidene microporous membranes are secured to each other by placing them in intimate contact and drying them on a drum dryer.

The rate of air flow through the microporous membrane of a gas outlet or a gas inlet can be tailored to the specific liquid transfer or delivery system of interest. The rate of air flow varies directly with the area of the membrane and the applied pressure. Generally, the area of the membrane is designed to enable the liquid transfer or delivery system to be primed in a required time under the conditions of use. For example, in medical applications it is desirable to be able to prime an intravenous set in from about 30 to about 60 seconds. In such applications as well as in other medical applications, the typical membrane may be in the form of a disc which has a diameter from about 1 mm to about 100 mm, preferably from about 2 mm to about 80 mm, and more preferably from about 3 mm to about 25 mm.

The pore size of the liquophilic and liquophobic microporous membranes is dependent on the liquid transfer or delivery system in which it is used, and, more particularly, whether the system is for medical or non-medical use. By way of illustration, where the gas inlet or gas outlet is to be incorporated in a system to be used for a medical application, the pore size of the liquophilic and liquophobic membranes is preferably selected so that at least one of the membranes provides a bacterial barrier to preclude entry of bacteria into the system. The pore size of the liquophilic and liquophobic microporous membranes may be the same or different. Generally the pore size of the liquophobic membrane is in the range of from about 0.02 to about 3 micrometers and the pore size of the liquophilic membrane is from about 0.04 to about 3 micrometers. Preferably the pore size of the membranes is below about 0.2 micrometers in order to maintain a suitable barrier to contaminants and bacteria.

It will be appreciated that the pressure required to transfer gas in or out of the processing system through the gas inlet or gas outlet of the present invention varies inversely with the pore size of the membrane. Accordingly, the choice of pore size may be determined by the application in which the gas inlet or gas outlet is used. For example, since the pressure required to pass gas through the gas outlet increases as the pore size of the membrane decreases, it may be desirable to choose a larger pore size (consistent with the other objectives of, for example, providing a bacterial barrier) where the delivery system is to be operated by hand so that the pressure required to use the system does not become too great for convenient hand use.

The housing may be constructed of rigid plastic material that is also transparent, such as polyethylene, an acrylic such as polymethyl methacrylate, polymethyl acrylate, polymethyl pentene-1, polyvinyl chloride, and vinyl chloride-vinylidene chloride copolymers. Translucent materials, such as polypropylene, polyethylene, urea-formaldehyde, and melamine-formaldehyde polymers, can also be employed. Other plastic materials that are particularly suitable are polystyrene, polyamides, polytetrafluoroethylene, polyfluorotrichloroethylene, polycarbonates, polyester, phenol-formaldehyde resins, polyvinyl butyral, cellulose acetate, cellulose acetate propionate, ethyl cellulose and polyoxymethylene resins. Polyacrylonitrile polybutadiene-styrene (ABS) is preferred. It is intended that the invention should not be limited by the type of housing being employed; other materials may be used, as well as mixtures, blends, and/or copolymers of any of the above.

A metal housing can be used. Suitable metals include stainless alloys, such as nickel, chromium, vanadium, molybdenum, and manganese alloys. The housing material should, of course, be inert to the liquids being processed.

The invention will be better understood by reference to the Figures. In these figures, like reference numerals refer to like parts.

Figure 4:
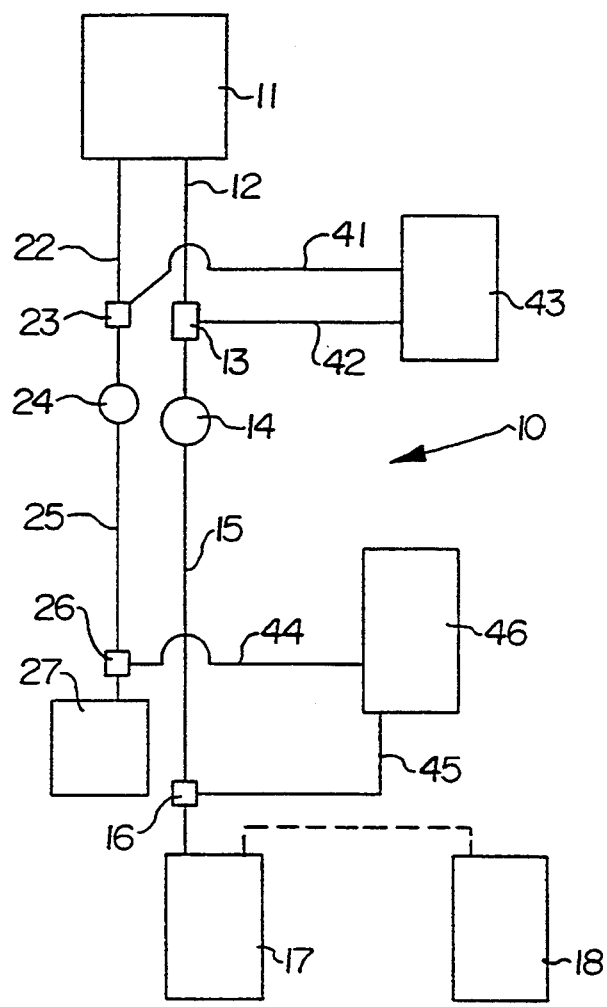
FIG. 4 is an embodiment of a blood processing system according to the invention, in which the gas from the system is recycled and stored for reuse.

FIGS. 1 through 5 show exemplary typical blood processing systems in accordance with the invention, generally denoted as 10. The blood processing set 10 includes a first container or blood collection bag 11, conduits 12 and 15, preferably flexible tubing, connecting the blood collection bag 11 and a second container (first satellite bag) 17 for receiving a blood product, such as PRP. A functional biomedical device 14 may be interposed between the collection bag 11 and the first satellite bag 17. As shown in FIGS. 2 and 4, collection bag 11 may also be connected via conduits 22 and 25, preferably flexible tubing, to a third container (second satellite bag) 27 for receiving a blood product, such as PRC; a functional biomedical device 24 may be interposed between the collection bag 11 and the second satellite bag 27. In another embodiment of the invention, the blood processing assembly 10 may also include an additional (third) satellite bag 18 for receiving a blood product, such as PC, which is connected to the first satellite bag 17 via a conduit, preferably flexible tubing. At least one seal, valve, or transfer leg closure or cannula (not illustrated) may also be positioned in the flexible tubing 12, 15, 22, and 25; this seal (or seals) is broken or opened when fluid is to be transferred between bags.

The blood processing assembly 10, with one or more satellite bags attached or connected via a conduit, may be used integrally or serially to separate components from whole blood.

It will be understood by those skilled in the art that the number and location of the gas inlet and gas outlet will depend upon the design criteria for the blood processing system. For example, more than one such gas inlet or gas outlet may be included in any or all of the conduits 12, 15, 22, and 25; one or more gas inlet and gas outlet may be included in the biomedical devices 14 and 24; and one or more gas inlet and gas outlet may be included in a blood or blood product container, or in a port or ports in such containers. In an embodiment of the invention in which a gas inlet 13 is positioned in conduit 12 and a gas outlet 16 is positioned in conduit 15, the gas inlet 13 is preferably placed as close to or in the first container as is practical in order to maximize the amount of blood product recovered in the conduit and the biomedical device; and the gas outlet 16 is preferably placed as close to the second container as practical in order to maximize the amount of air and gases purged from the system. It is intended that the invention is not to be limited by the number or placement of the gas inlet or gas outlet.

An embodiment of the invention includes a biological fluid administration assembly (illustrated in FIGS. 9a and 9b) having a functional biomedical device 14 defining a fluid flow path from an upstream end to a downstream end, and having a connector 91 on the upstream end and a conduit 15 on the downstream end. Disposed in the conduit 15 is a branching element 92 in fluid communication with the downstream end of the functional biomedical device, and having a connector 93 on a downstream portion thereof. A gas inlet 13 or a gas outlet 16, in accordance with the invention, is disposed in fluid communication with the branching element 92. A clamp 94 is preferably included, and is used to regulate the flow of a biological fluid or gas through the conduit. For example, if the functional biomedical device is a pre-primed filter, it may be desirable to close the clamp when inserting the administration assembly into a fluid processing assembly to avoid fluid loss during the connection procedure.

As has been noted above, it may be desirable to position a gas outlet as close to the downstream connector as possible in order to remove as much gas as is possible. Most desirable is removing all of the gas in the system. FIG. 9b illustrates an embodiment of the invention in which substantially all of the gas in the system is removed, and in which the gas outlet 16 is part of the connector 96. The connector has a body which defines a cavity, and a porous membrane for purging gas therethrough is positioned in the cavity. A sleeve on a downstream portion of the body may be included in the body for positioning a penetrating connector 95, such as a spike. Once the gas outlet is closed, clamped, or inactivated, the penetrating connector 95 may be used to pierce the porous membrane disposed in the body, thereby establishing a flow path through the connector 96 and into a downstream assembly or conduit.

Figure 6A:
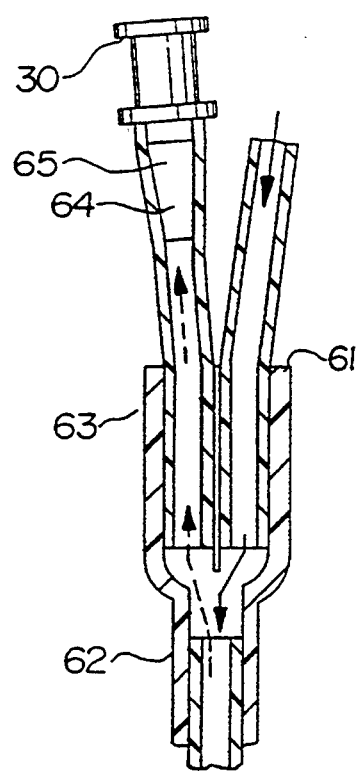
FIGS. 6A, 6B, and 6C are exemplary configurations of gas inlet and gas outlet according to the invention.
Figure 6B:
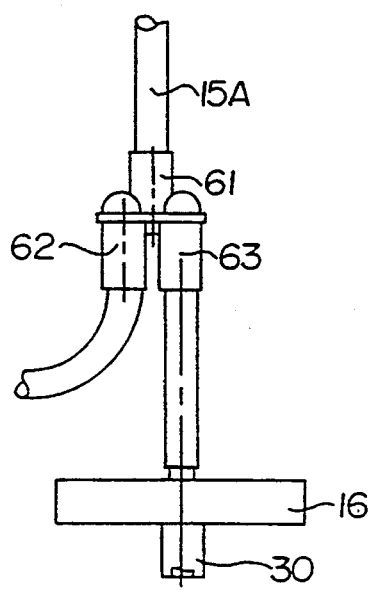
Figure 6C:
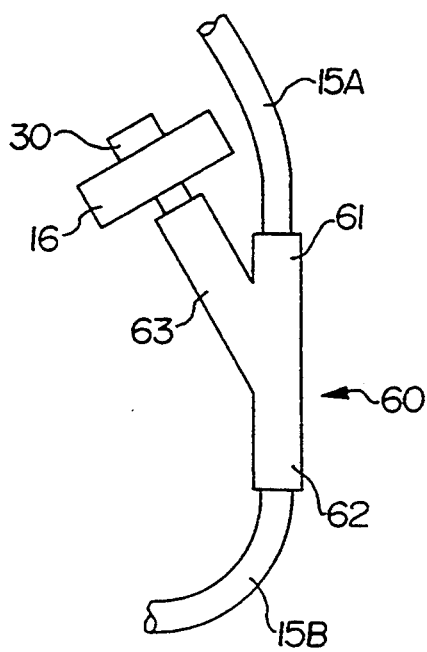

The gas inlet and gas outlet may be included in the system in any of a variety of ways depending on the choice of the designer. By way of example, when the gas inlet 13 and/or gas outlet 16 is to be included in a conduit, the gas inlet and gas outlet may be incorporated into branching element 60, such as a T-type connector (FIG. 9A) or a Y-type connector (FIG. 6C). As illustrated, the first leg 61 of branching element 60 accommodates a conduit through which blood enters the branching element 60. A second leg 62 of branching element 60 accommodates a downstream conduit. A gas inlet or, as outlet membrane is disposed in the third leg 63 of the branching element 60. The membrane may be liquophobic, liquophilic, or a multilayered combination of liquophobic and liquophilic layers. FIG. 6a shows a liquophilic layer 64 and a liquophobic layer 65.

Each of the remaining components of the assembly will now be described in more detail below:

The containers which are used in the blood processing assembly may be constructed of any material compatible with whole blood or blood products, and are capable of withstanding a centrifugation and sterilization environment. A wide variety of these containers are already known in the art. For example, blood collection and satellite bags are typically made from plasticized polyvinyl chloride, e.g., PVC plasticized with dioctylphthalate, diethylhexylphthalate, or trioctyltrimellitate. The bags may also be formed from a polyolefin, polyurethane, polyester, or polycarbonate.

As used herein, the tubing may be any conduit or means which provides fluid communication between the containers, and is typically made from the same flexible material as is used for the containers, preferably plasticized PVC. A seal, valve, or transfer leg closure is typically located within the tubing. A clamp or external closure device may also be used to regulate the flow of gas or blood product through a conduit. It is intended that the present invention is not limited by the type of material-used to construct the containers or the conduit which connects the containers.

As noted above, a functional biomedical device may be any of a number of devices. Various filters, separators, debubblers, and connectors are already known to practitioners in the art. In a preferred embodiment of the invention, the functional biomedical device includes one or more of the following: a platelet concentrator, a non-centrifugal platelet separatory device, and one or more leucocyte-depletion devices. Exemplary devices for use with red blood cells are disclosed in U.S. Pat. Nos. 4,925,572 and 4,923,620, the descriptions of which are herein incorporated by reference; an exemplary device for use with platelets is disclosed in U.S. Pat. No. 4,880,548, the description of which is herein incorporated by reference. The fibers used in the PRC device preferably have a critical wetting surface tension (CWST) above about 53 dynes/cm; for the platelet device, above about 70 dynes/cm. The fibers may be natural fibers or may be treated or modified in order to achieve or increase the CWST. Also, the fibers may be bonded, fused, or otherwise fixed to one another, or they may be mechanically entwined. Other porous media, for example, open cell foamed plastics, surface modified as noted above, may be similarly used.

FIG. 1 illustrates an embodiment of the closed, sterile blood processing system of the present invention wherein gas inlet and gas outlet are included in the conduits in sealed communication with the satellite bags. The blood processing assembly 10 includes a first container 11 for collecting or holding whole blood or a blood product and second container 17 for receiving a processed blood product, and conduits 12 and 15 interconnecting the first container and the second container. Interposed between the containers is a functional biomedical device 14. The illustrated embodiment includes a gas inlet 13 in conduit 12 upstream of biomedical device 14, and a gas outlet 16 in conduit 15 downstream of the biomedical device 14. In this embodiment, air may be added to the system through gas inlet 13 in order to recover blood or a blood product in conduit 12, biomedical device 14, and conduit 15. In this embodiment, gas in conduits 12 and 15 and biomedical device 14 is separated from the blood product through gas outlet 16 and the separated gas is vented from the system. The gas inlet 13 is preferably carried in conduit 12 as close as practical to first container 11 in order to maximize the recovery of blood product. The gas outlet is preferably carried in conduit 15 as close as is reasonably possible to satellite bag 17 to maximize the volume of gas vented from the system, and concomitantly to minimize the volume of gas transferred into the satellite bag. In another embodiment of the invention, illustrated in FIG. 3, sterile air or gas may be retained in air container 32 until ready for use, at which point the gas is transferred into the system 10 through conduit 31 and gas inlet 13. As illustrated, the blood processing system 10 may also include a second air container 34 for holding air displaced from the system 10 through gas outlet 16 and conduit 33. An embodiment of the invention, illustrated in FIG. 3B, includes a single gas container 35, which serves as both a source and repository of gas or air. Gas may enter conduit 12 through gas inlet 13 by passing through conduit 37. Gas may be purged from the assembly through gas outlet 16 through conduit 36.

In another embodiment of the invention, illustrated in FIG. 2, the blood processing system comprises multiple bags and multiple transfer lines. The fluid pathway that leads from first container 11 to second container 17 is exemplary of a typical PRP processing configuration. The fluid pathway that leads-from first container 11 to third container 27 is exemplary of a typical PRC processing configuration. Similar to the previously described fluid pathways, the illustrated pathway includes first container 11 for collecting or holding whole blood or a blood product and third container 27 (for receiving a processed blood product), and a conduit 22 and 25 interconnecting the first container and the third container. Interposed between the containers is a functional biomedical device 24. The illustrated embodiment includes a gas inlet 23 in conduit 22 upstream of biomedical device 24, and a gas outlet 26 in conduit 25 downstream of the biomedical device 24. FIG. 4 is similar to FIG. 3 in the inclusion of first air container 43 for adding air/gas to the system 10 and second air container 46 for holding air transferred out of the system 10. As illustrated, first air container 43 may supply air/gas to the system through conduit 41 and gas inlet 23, as well as through conduit 42 and gas inlet 13. As illustrated, gas may be removed from the system 10 into second air container 46 through gas outlet 26 and conduit 44, as well as through gas outlet 16 and conduit 45. Fourth container 18 is included to illustrate that other containers may be included in the blood processing system 10.

In an embodiment of the invention, a gas inlet or a gas outlet are capable of being penetrated, aseptically as for example, by a syringe or the like, to permit sterile gas to be injected into the system through the membrane to facilitate the recovery of entrapped blood components in the system, or to draw gas or air from the system. For example, FIG. 9b shows a gas outlet 16 as part of connector 96. Connector 96 is positioned in the downstream end of conduit 15, and includes gas outlet 16 and a sleeve for accommodating a penetrating connector 95.

In another embodiment of the invention, the assembly does not include any containers, but does include the elements for establishing a flow path which utilizes a gas inlet and/or a gas outlet. An example of these assemblies is illustrated in FIG. 5. The assembly 10 includes a penetrating connector 50 on one end and a receiving connector 51 on the other. Interposed between the connectors 50 and 51 are a conduit 12, gas inlet 13, functional biomedical device 14, conduit 15, and gas outlet 16. Gas inlet 13 is preferably positioned in conduit 12 as close to connector 50 as practical, and gas outlet 16 as close to connector 51 as practical.

Figure 10:
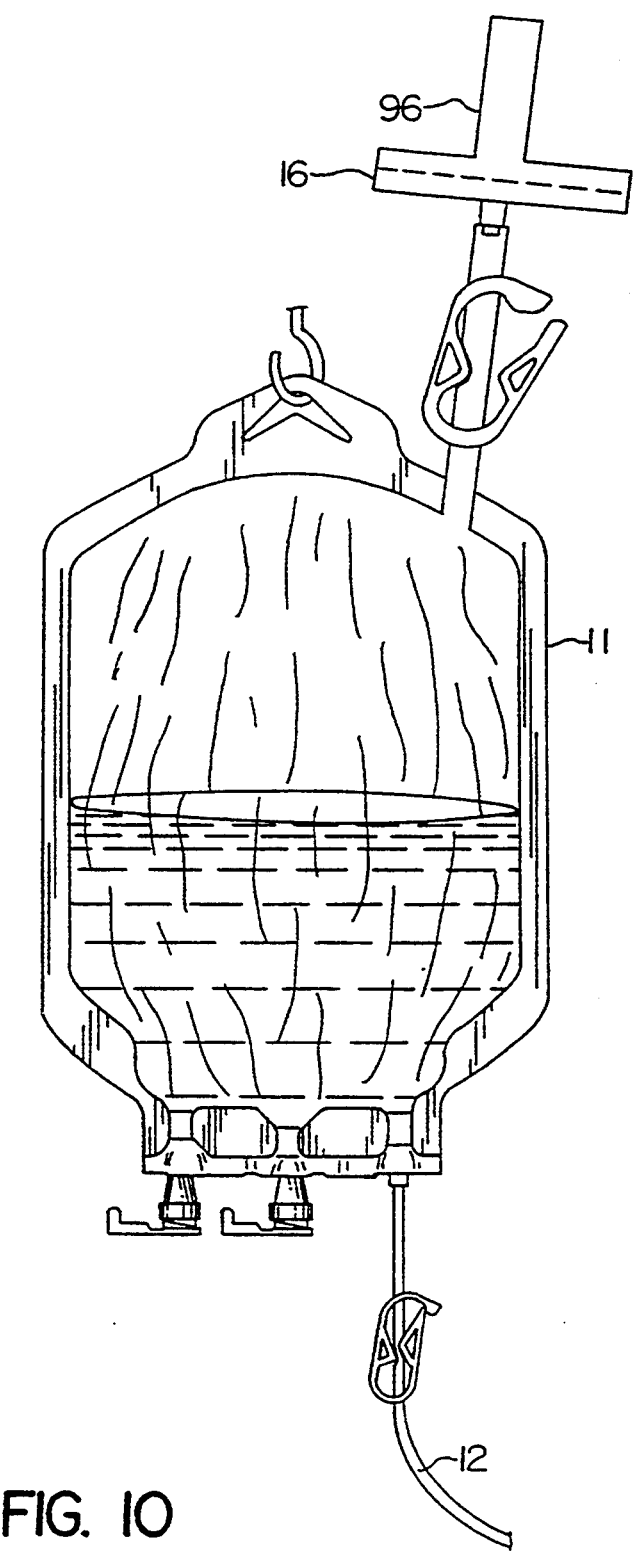
FIG. 10 is a collection bag communicating with a gas inlet.

In another embodiment of the invention, illustrated in FIG. 10, a gas inlet 16 is cooperatively arranged with a collection receptacle 11. A clamp, closure, or other means may be used for opening and closing access to the receptacle. As illustrated, the gas inlet 16 is part of a connector 96 should it be desirable to establish communication between the gas inlet and a gas source. When making the connection to another element, such as an air container, it is preferable that the membrane in the gas inlet is not pierced by the mating connector.

It will be appreciated that the invention may be modified to-include recovery and recycle of the gas in the system, or it may be modified to include a separate gas purge reservoir as discussed above (see FIGS. 3 and 4).

One skilled in the art will recognize that the invention as described here may be reconfigured into different combinations. These different configurations and combinations are included within the scope of the invention.

In general, the donor's blood is received directly into the blood collection bag 11, which may be connected to a satellite bag 17 for PRP and/or a satellite bag 27 for PRC. Preferably, the PRP satellite bag is in turn connected to a satellite bag 18 for PC.

Movement of blood or a blood product through the system is effected by maintaining a pressure differential between the collection bag and the destination of the blood or the blood product (e.g., a satellite bag or a needle on the end of a conduit). Exemplary means of establishing this pressure differential may be by gravity head, applying pressure to the collection bag (e.g., by hand or with a pressure cuff), or by placing the satellite bag in a chamber which establishes a pressure differential between the satellite bag and the collection bag (e.g., a vacuum chamber).

Once the pressure differential is established and any clamps are opened, a column of blood or blood product is driven through conduit 15 or 25, through functional biomedical device 14 or 24, into conduit 12 or 22, and into the first leg 61 of branching element 60. A clamp is placed between satellite bag 17 or 27 and gas outlet 16 or 26. As the blood or blood product advances, it pushes gas in the conduit ahead of it until the gas reaches branching element 60. At branching element 60, gas ahead of the liquid column moves into the third leg 63 of branching element 60 and is vented from the system through gas outlet 16 or 26. As the liquid in conduit 15a or 25a continues its travel through the second leg 62 of branching element 60 and into conduit 15 or 25 leading from branching element 60 to receiving container 17 or 27, gas in conduit 15 or 25 is displaced toward and into the third leg 63 of branching element 60 where it passes out of the blood processing system through first layer 64, second layer 65, and cap 30 of gas outlet 16 or 26; As gas in conduit 15a or 25a is displaced by advancing liquid, the liquid being transferred fills conduit 15b or 25b with liquid. After conduit 15b or 25b is filled with liquid, third leg 63 of branching element 60 also fills with liquid. The liquid then contacts and wets the first layer 64 of gas outlet 16 or 26. Wetting of first layer 64 by the liquid seals or inactivates gas outlet 16 or 26 to the passage of gas and thus forecloses air from outside the system from entering into the system through gas outlet 16 or 26.

A clamp is normally closed in order to allow gas in the conduit 15a, functional biomedical device 14, and gas outlet 16 to be purged from the system 10, and to prevent gas in the system from entering satellite bag 17. After the entire conduit line has been primed, the clamp is opened to allow blood product to flow into satellite bag 17.

In operation, as a column of blood and/or blood product flows from the first container 11 through the conduit means 12 or 22 and the biomedical device 14 or 24 toward the satellite bag 17 or 27, it pushes gas in those elements toward branching element 60. At branching element 60, gas ahead of the column of blood and/or blood component moves into the third leg 63 of branching element 60. Since the gas passes through the liquophobic porous medium, but the blood and/or blood products do not, the gas is separated from the blood products and is precluded from entering the satellite bag. The gas outlet may comprise a liquophobic porous medium having a pore size of not greater than 0.2 microns and may be included in one leg of a branching connector.

The gases separated by the gas outlet 16 or 26 may be vented from the system, or they may be collected in gas container 35 (as noted below) and returned to the system as a purge gas to facilitate the recovery of blood and blood product that becomes trapped in the various components of the system.

After the system is primed and the gas outlet is inactivated, the clamp adjacent to the satellite bag 17 or 27 is opened to allow the satellite bag to fill with processed blood product. This continues until container 11 collapses. In order to recover the very valuable blood product retained in the system, ambient air or a sterile gas may enter the system through gas inlet 13 or 23. If gas inlet 13 or 23 is a manual inlet means, a closure is opened or a clamp released; if the gas inlet 13 or 23 is automatic, the pressure differential between-the gas inlet and satellite bag 17 or 27 will cause the air or gas to flow through conduit 12 or 22, through biomedical device 14 or 24, and toward satellite bag 17 or 27. In the process, retained blood or blood product that is trapped in those elements during processing are recovered from those components and collected in satellite bag 17 or 27. It should be noted that the purge air or gas is preferably separated from the blood product at gas outlet 16 or 26, so that little, if any, purge gas will be received by satellite bag 17 or 27. This may be accomplished by clamping the conduit 15b or 25b downstream of the gas outlet 16 or 26. In another embodiment of the invention, the purge air or gas may be separated from the system through a gas outlet located in the bag itself. Under typical conditions, the blood or blood product will drain through the system until flow is stopped. In a typical device, the flow may stop when about half of the functional biomedical device is emptied.

It will be appreciated that when the blood or blood product from the donor bag 11 is expressed to the satellite bags 17 and 27, some of the blood or blood product may be trapped in conduits 12, 15, 22, and 25 and in biomedical devices 14 and 24. For example, 8 cc to 35 cc is typically retained in the system; but as little as 2 cc to as much as 150 cc or more may be retained in some types of systems. In an embodiment of the invention, air or gas may be stored in gas container 32, 53, or 43; upon opening of valve or clamp means in conduits 31, 37, 41, or 42, gas can be fed through conduits 31, 37, 41 or 42 to purge conduits 12 and 22, and biomedical devices 14 and 24, thereby facilitating the recovery of blood components that may have been trapped in the conduits and biomedical devices during processing.

Preferably, the purge air or gas is fed to conduits 12 and 22 at a point as close as is reasonably possible to blood receiving bag 11 to maximize the volume of blood component recovered. Air or gas container 32, 35, or 43 is preferably flexible so that the gas therein may be fed to the system merely by simple compression. Container 11, air or gas container 32, 35, or 43, and satellite bags 17, 18, or 27 may be composed of the same material.

In another embodiment of the invention, a purge gas reservoir 35 is provided. Purge gas reservoir 35 is in sealed communication with blood receiving bag 11 through valve or clamp means in conduits 36 and 37.

Purge gas reservoir 35 is preferably flexible so that gas therein may be fed to the system merely by simple compression, and the bag may be made of the same materials as are container 11 and satellite bags 17, 27.

After the blood in receiving bag 11 is processed, valve or clamp means in conduit 37 is opened, and purge gas reservoir 34, 35, or 46 is compressed to feed purge gas into the system through conduits 15, 22 and 25. As noted above, the purge gas is fed to the conduits preferably as close to blood receiving bag 11 as is reasonably possible. The purge gas is preferably fed through membrane means in association with conduits 31, 37, 41, and 42.

Figure 7:
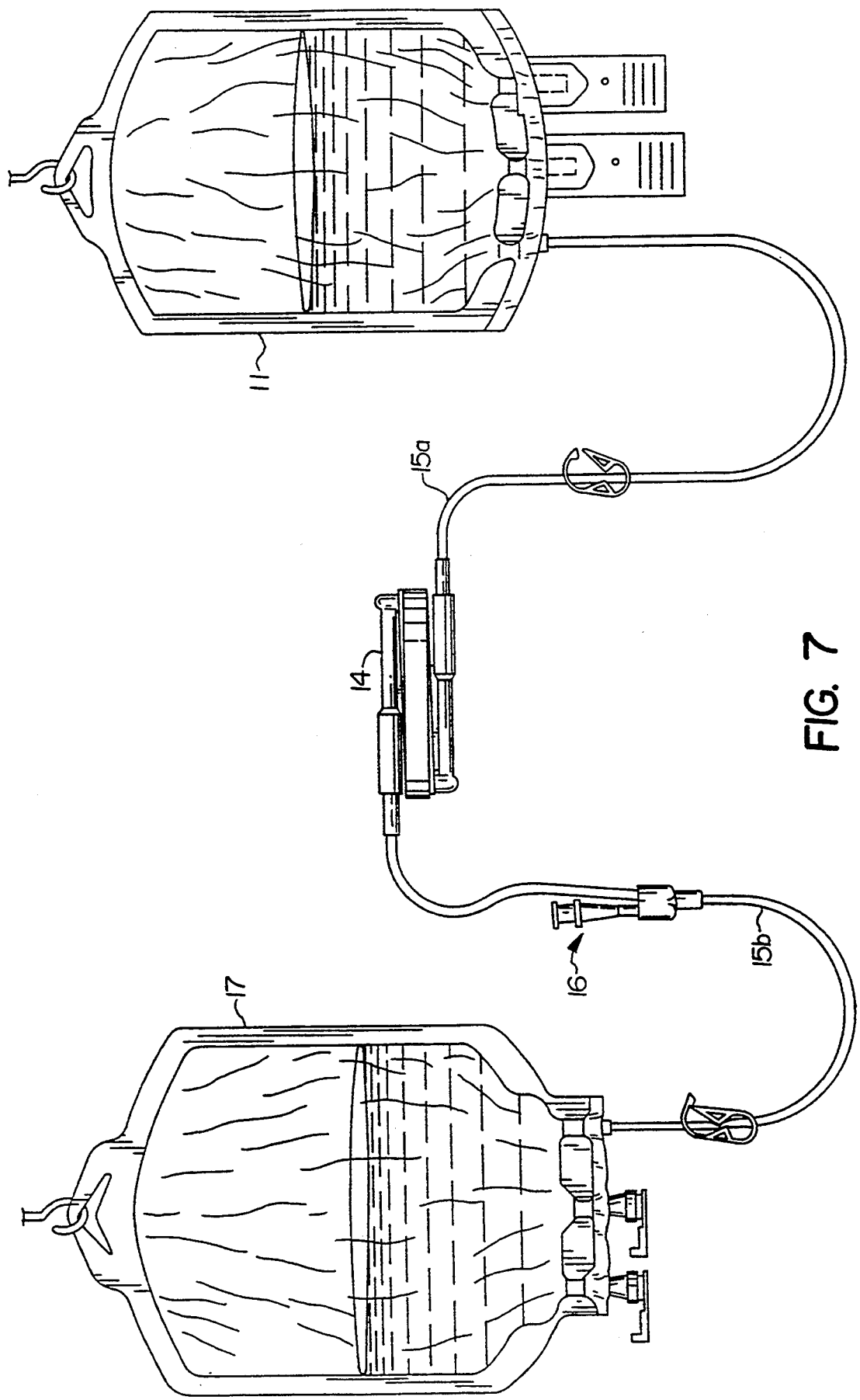
FIG. 7 is a vertical sectional view of an embodiment of a gas outlet according to the invention.
Figure 8:
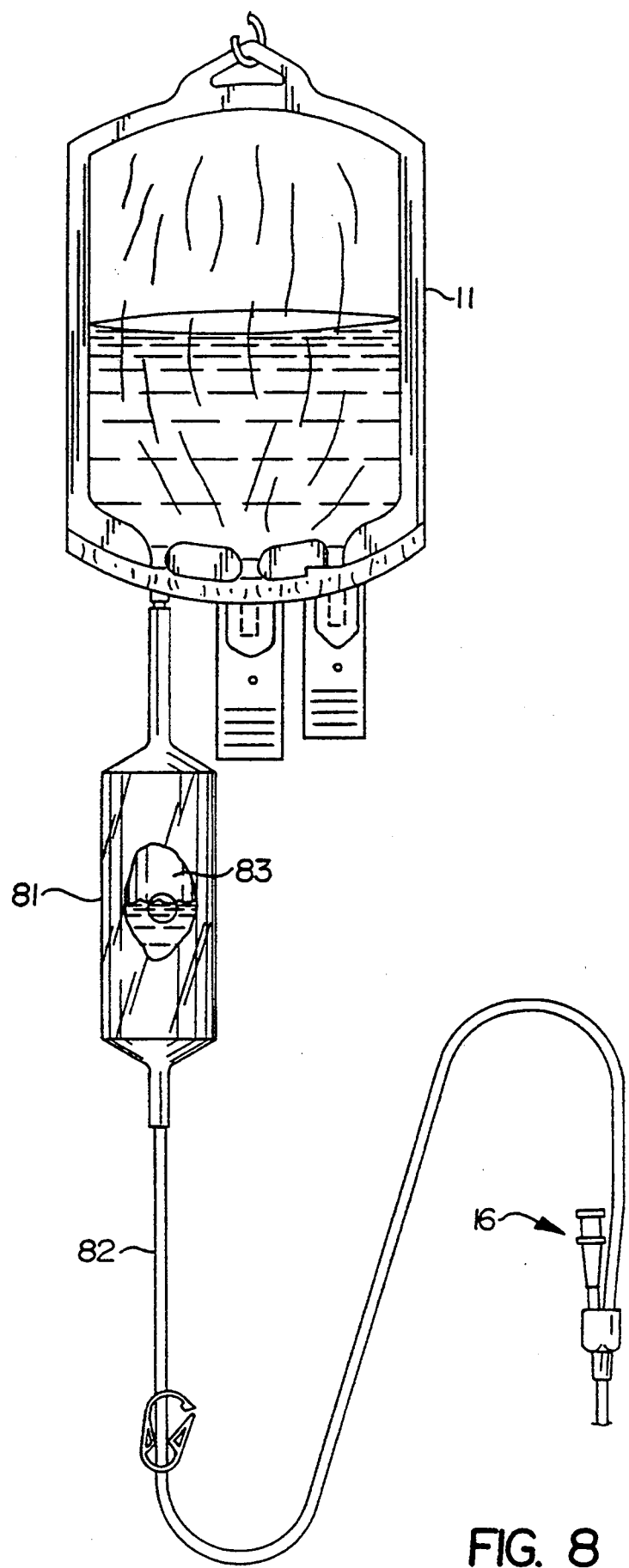
FIG. 8 is a perspective view of an intravenous feeding system, including gas outlet for the passage of gas from the administration set.

It will be appreciated that gas outlet 16 and 26 can also be used to prime a liquid transfer or delivery system which is used for the percutaneous injection of liquids into a patient. Such systems, including, for example, an intravenous injection system as illustrated in FIG. 7, comprise a collapsible container 11 which contains the liquid to be transferred or delivered, a drip chamber 81 for indicating or monitoring the flow of liquid injected into the patient, and a conduit 82 in communication with the container 11 and drip chamber 81 and leading from drip chamber 81 to the injection needle or the like (not shown). In accordance with this embodiment of the present invention, gas outlet 16 as described above is carried in conduit 82 downstream of drip chamber 81 but upstream of the terminal end of conduit 82.

To prime the system, container 11 is collapsed sufficiently to drive a column of liquid into the drip chamber 81 which has an air space 83 therein, which has been created, for example, by briefly inverting the drip chamber 81. The moving column of liquid from drip chamber 81 drives a head of gas in the portion of conduit 82 extending from drip chamber 81 toward the terminal end of conduit 82. When the head of gas reaches gas outlet 16, it is passed out of conduit 82 in the same manner as described above.

It will be understood that while the invention has been described in connection with the preferred embodiment, alternative embodiments are also possible. For example, it is possible for blood collection bags to receive blood components from one of the satellite bags, if desirable, and it is likewise within the contemplation of the invention to use satellite bags that are partitioned internally and are capable of receiving different blood component in the same satellite bag.

What is claimed is:

1. A filtration system for the filtration of blood or a blood component comprising:
   a container for containing the blood or the blood component to be filtered;
   a receiving container for receiving the filtered blood or the blood component;
   a transfer line communicating between said container for the blood or the blood component to be filtered and said receiving container;
   a leukocyte depletion filter capable of filtering said blood or said blood component carried in said transfer line between said container for the blood or the blood component to be filtered and said receiving container; and
   a gas outlet carried in said transfer line downstream of said filter and upstream of said receiving container, said gas outlet including:
   (a) a housing;
   (b) a first microporous membrane having first and second sides and being positioned in said housing with said first side in communication with said transfer line, said first microporous membrane being wettable by the filtered blood or the filtered blood component; and
   (c) a second microporous membrane superimposed on said second side of said first microporous membrane, said second microporous membrane being capable of permitting gas to pass therethrough, said first and second microporous membranes arranged to permit the gas to be vented from the gas outlet while said first microporous membrane remains unwetted with blood or blood component, and to permit said gas outlet to be sealed when said first microporous membrane is wetted with blood or blood component.

2. The system of claim 1 wherein said first microporous membrane and said second microporous membrane comprise a polymeric material selected from the group consisting of a polyamide, polyvinylidene difluoride and polytetrafluoroethylene.

3. The system of claim 1 wherein said first microporous membrane and said second microporous membrane comprise polyvinylidene difluoride.

4. The system of claim 1 wherein the pore size of said first and said second microporous membrane is in the range of from about 0.02 to about 3.0 microns.

5. The system of claim 1 comprising a closed, sterile system.

6. The system of claim 1 further comprising at least one gas inlet including a microporous membrane, interposed between the container for containing blood or blood product to be filtered, and the leukocyte depletion filter.

7. The system of claim 1 wherein the gas inlet and gas outlet block the entry of bacteria into the system.

8. The system of claim 6 wherein the gas inlet comprises a liquophobic microporous membrane.

9. The system of claim 6 wherein the leukocyte depletion filter includes a gas inlet.

10. The system of claim 6 comprising a closed sterile system, wherein the microporous membranes of the gas inlet and the gas outlet each comprise at least one sheet, and wherein the leukocyte depletion filter includes a leukocyte depletion medium comprising fibers, said medium having a CWST of above about 53 dynes/cm.

11. The system of claim 1 wherein the gas outlet has a pore rating of less than about 3 microns.

12. The system of claim 11 wherein the gas outlet has a pore rating of about 0.2 microns or less.

13. A closed system for the transfer of a biological fluid comprising:
   a collapsible reservoir which contains the biological fluid to be transferred;
   a receiving container for receiving the transferred biological fluid:
   a transfer line in communication with said collapsible reservoir and with said receiving container;
   a leukocyte depletion filter capable of leukocyte depleting said biological fluid carried in said transfer line between said reservoir and said receiving container;
   and
   a gas outlet carried in said transfer line downstream of said filter and upstream of said receiving container, said gas outlet including:
   (a) a housing;
   (b) a first microporous membrane having first and second sides and being positioned in said housing with said first side in communication with said transfer line, said first microporous membrane being liquid-wettable by the biological fluid to be transferred in said system; and (c) a second microporous membrane superimposed on said second side of said first microporous membrane, said second microporous membrane being capable of permitting gas to pass therethrough, said first and second microporous membranes arranged to permit, the gas to be vented from said gas outlet while said first microporous membrane remains unwetted with biological fluid, and to permit said gas outlet to be sealed when said first microporous membrane is wetted with biological fluid.

14. The system of claim 13 wherein said first microporous membrane and said second microporous membrane comprise a polymeric material selected from the group consisting of a polyamide, polyvinylidene difluoride and polytetrafluoroethylene.

15. The system of claim 13 wherein said first microporous membrane and said second microporous membrane comprise polyvinylidene difluoride.

16. The system of claim 13 wherein the pore size of said first and said second microporous membrane is in the range of from about 0.02 to about 3.0 microns.

17. The system of claim 13 comprising a closed sterile system.

18. The system of claim 13 further comprising at least one gas inlet including a microporous membrane, carried in said transfer line upstream of said leukocyte depletion filter and downstream of said collapsible reservoir.

19. The system of claim 18 wherein the gas inlet allows gas to enter the system, and the gas outlet allows gas to exit the system, and said gas inlet and said gas outlet block the entry of bacteria into the system.

20. The system of claim 19 wherein the each of said membranes in said gas inlet and said gas outlet comprises a polymeric material selected from the group consisting of a polyamide, polyvinylidene difluoride and polytetrafluorethylene.

21. The system of claim 19 wherein said system is suitable for leukocyte depleting biological fluid comprising blood or a blood product.

22. The system of claim 19 wherein the leukocyte depletion filter includes a leukocyte depletion medium comprising fibers, said medium having a CWST of above about 53 dynes/cm.

23. The system of claim 22 wherein the leukocyte depletion medium comprises fibers, said medium having a CWST of above about 70 dynes/cm.

24. A method for processing a biological fluid comprising:
passing a biological fluid through a leukocyte depletion device;
opening at least one gas inlet comprising a porous medium; and
driving the biological fluid through the leukocyte depletion device by allowing gas to flow into the gas inlet.

25. The method of claim 24 further comprising opening a gas inlet coupled to the leukocyte depletion device.

26. The method of claim 24 including opening a gas inlet upstream from the leukocyte depletion device.

27. The method of 26 further comprising opening a gas inlet coupled to the leukocyte depletion device.

28. The method of claim 24 comprising passing red cells through a leukocyte depletion device including a fibrous filter having a CWST of above about 53 dynes/cm.

29. The method of claim 24 comprising passing platelets through a leukocyte depletion device including a fibrous filter having a CWST of above about 70 dynes/cm.

30. The method of claim 24 further comprising collecting the biological fluid passing through the leukocyte depletion device in a container downstream of the device.

31. The method of claim 24 wherein processing biological fluid comprises passing blood or a blood product through the leukocyte depletion medium, and allowing gas to flow into a gas inlet that blocks the entry of bacteria.

32. The method of claim 24 wherein allowing gas to flow into the gas inlet comprises passing the gas through a microporous membrane that prevents bacteria from passing therethrough.

33. The method of claim 32 wherein the microporous membrane comprises a liquophobic membrane.

34. The method of claim 33 wherein the membrane comprises a polymeric material selected from the group consisting of a polyamide, polyvinylidene difluoride and polytetrafluorethylene.

35. The method of claim 33 wherein the membrane comprises nylon 66.

36. The method of claim 24 wherein allowing gas to pass through the inlet comprises passing the gas through a liquophobic porous medium having a pore rating of less than about 3 microns.

37. The method of claim 36 wherein the liquophobic porous medium comprises a membrane having a pore rating of about 0.2 microns or less.

38. The method of claim 24 wherein passing the biological fluid through a leukocyte depletion device comprises passing blood or a blood product through the device, and wherein opening at least one inlet comprises:
opening a gas inlet upstream of the leukocyte depletion device, driving the blood or blood product through the device by allowing gas to flow into the gas inlet, without passing bacteria through the gas inlet; and
opening a gas inlet coupled to the leukocyte depletion device, driving the blood or blood product through the device by allowing gas to flow into the gas inlet, without passing bacteria through the gas inlet;
said method further comprising:
collecting the leukocyte depleted blood or blood product in a container downstream of the leukocyte depletion device.

39. A method for processing blood or a blood product comprising:
passing the blood or blood product through a leukocyte depletion medium;
passing gas displaced by the blood or blood product through a gas outlet comprising a porous medium until the blood or blood product contacts the porous medium; and,
passing gas through a gas inlet comprising a porous medium to drive additional blood or blood product through the leukocyte depletion medium.

40. The method of claim 39 wherein the blood or blood product is processed in a closed sterile system.

41. The method of claim 39 wherein the porous medium of the gas outlet includes a liquophilic microporous membrane and a liquophobic microporous membrane, and wherein passing gas through the gas outlet comprises passing gas through the liquophilic membrane and then through liquophobic membrane until the blood or blood product wets the liquophilic microporous membrane and the gas outlet is sealed.

42. The method of claim 39 wherein passing gas through said gas outlet comprises passing gas through a porous medium having a pore rating of about 0.2 microns or less, and passing gas through said inlet comprises passing gas through a porous medium having a pore rating of about 0.2 microns or less.

43. The method of claim 39 wherein the gas inlet and the gas outlet each comprise a porous medium comprising a polymeric material selected from the group consisting of a polyamide, polyvinylidene difluoride and polytetrafluorethylene.

44. The method of claim 39 wherein passing gas through said gas outlet comprises passing gas through a porous medium comprising a membrane sheet that blocks the passage of bacteria, and passing gas through said gas inlet comprises passing gas through a porous medium comprising a membrane sheet that blocks the passage of bacteria.

45. A system for processing blood or a blood component comprising:
a leukocyte depletion filter;
a container for receiving leukocyte depleted blood or blood component, said container located downstream of the filter;
a gas collection arrangement in fluid communication with the upstream of the filter and the downstream of the filter, said gas collection arrangement including a gas container and a porous medium for passing gas therethrough, said porous medium comprising a membrane liquophobic to the blood or the blood component.

46. The system of claim 45 further comprising an additional container upstream of the filter.

47. The system of claim 46 comprising a closed sterile system.

48. The system of claim 45 wherein the membrane comprises a polymeric material selected from the group consisting of a polyamide, polyvinylidene difluoride and polytetrafluorethylene.

49. The system of claim 45 wherein porous medium for passing gas further comprises a membrane liquophilic to the blood or blood component.

50. The system of claim 45 wherein the porous medium for passing gas has a pore rating of less than about 3 microns.

51. The system of claim 50 wherein the gas container is compressible.

52. The system of claim 50 wherein the gas container is capable of receiving gas displaced by the blood or blood product passing through the downstream of the leukocyte depletion filter.

53. The system of claim 52 wherein the gas container is capable of transferring gas to the upstream of the leukocyte depletion filter.

54. The system of claim 45 wherein the porous medium for passing gas has a pore rating of about 0.2 microns or less.

55. The system of claim 45 wherein the gas container comprises a flexible container.

56. The system of claim 45 wherein the gas collection arrangement includes two conduits.

57. The system of claim 45 wherein the porous medium for passing gas is interposed between the gas container and the upstream of the leukocyte depletion filter.

58. The system of claim 51 wherein the gas collection arrangement further comprises a clamp interposed between the gas container and the upstream of the filter, and a clamp interposed between the gas container and the downstream of the filter.

59. The system of claim 57 wherein the leukocyte depletion filter includes a leukocyte depletion medium comprising fibers, said fibrous medium having a CWST of at least about 53 dynes/cm.

60. The system of claim 59 wherein the fibrous medium has a CWST of at least about 70 dynes/cm.

* * * * *

UNITED STATES PATENT AND TRADEMARK OFFICE
CERTIFICATE OF CORRECTION

PATENT NO. : 5,451,321
DATED : September 19, 1995
INVENTOR(S) : Matkovich

It is certified that error appears in the above-indentified patent and that said Letters Patent is hereby corrected as shown below:

Column 18, Line 34, change "1" to --6--;

Line 55, change ":" to --;--;

Column 19, Line 27, delete "closed";

Column 22, Line 15, change "50" to --51--;

Line 32, change "51" to --57--.

Signed and Sealed this

Twenty-fifth Day of June, 1996

Attest:

BRUCE LEHMAN

*Attesting Officer*    *Commissioner of Patents and Trademarks*